United States Patent
De La Poterie

(10) Patent No.: US 7,351,405 B2
(45) Date of Patent: Apr. 1, 2008

(54) LONG-LASTING COSMETIC COMPOSITION FOR APPLICATION TO HUMAN HAIR, SUCH AS EYELASHES AND EYEBROWS

(75) Inventor: Valerie De La Poterie, Le Chatelet en Brie (FR)

(73) Assignee: L'Oreal, Paris (FR)

( * ) Notice: Subject to any disclaimer, the term of this patent is extended or adjusted under 35 U.S.C. 154(b) by 843 days.

(21) Appl. No.: 10/119,013

(22) Filed: Apr. 10, 2002

(65) Prior Publication Data

US 2002/0187116 A1 Dec. 12, 2002

(30) Foreign Application Priority Data

Apr. 10, 2001 (FR) .................................. 01 04886

(51) Int. Cl.
*A61Q 1/10* (2006.01)
(52) U.S. Cl. ................................ 424/70.7; 424/70.11
(58) Field of Classification Search ............. 424/70.7, 424/401, 63, 70.1, 70.11
See application file for complete search history.

(56) References Cited

U.S. PATENT DOCUMENTS

| | | | |
|---|---|---|---|
| 4,423,031 A | | 12/1983 | Murui et al. .................. 424/63 |
| 4,988,502 A | * | 1/1991 | Ounanian et al. ............. 424/63 |
| 5,053,221 A | * | 10/1991 | Robertson et al. ............ 424/63 |
| 5,753,215 A | * | 5/1998 | Mougin et al. .......... 424/70.11 |
| 5,843,417 A | * | 12/1998 | Hanna et al. .............. 424/70.7 |
| 5,846,550 A | * | 12/1998 | Perrin et al. ................ 424/401 |
| 5,911,973 A | * | 6/1999 | de la Poterie ................ 424/61 |
| 5,955,003 A | * | 9/1999 | Terren et al. ............... 424/401 |
| 6,001,374 A | * | 12/1999 | Nichols ...................... 424/401 |

(Continued)

FOREIGN PATENT DOCUMENTS

EP 0745372 12/1996

(Continued)

OTHER PUBLICATIONS

Synthetic Specialties Company, "Sekisui Techpolymer Microspheres", www.syntheticspecialties.com/sekisui_techpolymer_microspheres.htm, Accessed Jan. 31, 2007, pp. 1-2.*

(Continued)

*Primary Examiner*—Sharon E. Kennedy
(74) *Attorney, Agent, or Firm*—Oblon, Spivak, McClelland, Maier & Neustadt, P.C.

(57) ABSTRACT

The invention relates to mascara compositions. In one embodiment, it relates to a dye-free and wax-free mascara composition that lasts more than one day when applied to eyelashes, is resistant to water, and does not noticeably thicken eyelashes on application. In another embodiment, it relates to a wax-free mascara composition comprising solid particles of a film-forming acrylic polymer dispersed in a cosmetically acceptable aqueous medium, in which the film-forming acrylic polymer are capable of forming a film having a water-uptake, after immersion for 10 minutes in water at 25° C., of less than 25 wt. %, and wherein the composition has a viscosity, measured at 25° C., at a shear rate of 200 s$^{-1}$, of from 4 Pa·s to 18 Pa·s. In other embodiments, the invention relates to make-up kits, articles, and methods for making-up and/or coloring human hair, such as eyelashes and/or eyebrows, using these compositions.

30 Claims, 1 Drawing Sheet

U.S. PATENT DOCUMENTS

| | | | |
|---|---|---|---|
| 6,132,736 A * | 10/2000 | Mellul et al. | 424/401 |
| 6,306,411 B1 * | 10/2001 | Jager Lezer | 424/401 |
| 6,375,941 B1 * | 4/2002 | Piot et al. | 424/70.7 |
| 6,458,390 B1 * | 10/2002 | Manelski et al. | 424/617 |
| 6,534,047 B1 * | 3/2003 | Bodelin | 424/70.7 |
| 6,726,900 B2 * | 4/2004 | Scancarella et al. | 424/64 |

FOREIGN PATENT DOCUMENTS

| | | |
|---|---|---|
| EP | 0875243 | 11/1998 |
| EP | 1018334 | 7/2000 |
| EP | 1066819 | 1/2001 |
| EP | 1101488 | 5/2001 |
| EP | 1163898 | 12/2001 |
| WO | WO 96/33690 | 10/1996 |

OTHER PUBLICATIONS

Sekisui Plastics Co., LTD., "Nanospherical polymer particle, What is Techpolymer?", www.tech-p.com/english/product/development/biconvex.html, Copyright 2005, pp. 1-4.*

Sekisui Plastics Co., LTD:, "Developmental and technical information (Film)", www.tech-p.com/english/application/filmcompounding/index.html, Copyright 2005, pp. 1-2.*

Sekisui Plastics Co., LTD., "Developmental and technical information (Cosmetics)", www.tech-p.com/english/application/cosmetic/index.html, Copyright 2005, pp. 1-2.*

Noveon, Inc., "Avalure® Film Forming Polymers for Personal Care Applications," www.personalcare.noveon.com/TechnicalDataSheets/tds248.pdf, Feb. 10, 2006, pp. 1-3.*

* cited by examiner

LONG-LASTING COSMETIC COMPOSITION FOR APPLICATION TO HUMAN HAIR, SUCH AS EYELASHES AND EYEBROWS

BACKGROUND OF THE INVENTION

1. Field of the Invention

The present invention relates to mascara compositions for making up human eyelashes and/or eyebrows, comprising an acrylic polymer aqueous dispersion. The invention also relates to a method for making up human eyelashes and/or the eyebrows.

2. Background of the Invention

Mascaras are commonly prepared as one of two types of wax-based formulations. The first type are aqueous mascaras, known as cream mascaras. These are in the form of an emulsion of waxes in water. The second type are anhydrous mascaras or mascaras with a low water content, known as waterproof mascaras. These are in the form of a dispersion of waxes in volatile organic solvents.

It is also known that film-forming polymers, that may be dissolved or dispersed in an aqueous medium, can be used with waxes. See, FR-A-2 528 699 and EP-A-655 234. However, the make-up film obtained after applying these mascaras does not exhibit sufficient cohesion, because the waxes make the film brittle. The film is thus not sufficiently resistant to friction, especially to contact with fingers. It is also not sufficiently resistant to water, for example when to tears or sweat or when worn while bathing or taking a shower. This mascara has a tendency to be worn away over time: grains become deposited leaving marks around the eye. The make-up does not stay on well over time: it cannot be kept on for more than a day. The user must thus apply the mascara at least once a day to maintain a satisfactory make-up result on the eyelashes.

Some users wish to have eyelashes that are well colored but not thickened. It is possible to color eyelashes by using a dye containing colorants, similar to hair dyeing. However, this type of dyeing is generally carried out at a beauty salon because special techniques need to be used. This results in constraints for the user.

There is therefore a need for a mascara composition enabling the user to color her eyelashes easily without thickening them.

The aim of the present invention is thus to provide a mascara composition giving a natural make-up result that stays on well over time, for longer than a day, or even two days or more, and which can be used to color human hair, such as eyelashes and eyebrows.

SUMMARY OF THE INVENTION

Accordingly, it is an object of the present invention to provide a long-lasting mascara for use on human hair, such as eyelashes or eyebrows.

It is another object of the present invention to provide a long-lasting mascara composition that colors human hair, such as eyelashes or eyebrows, and can be easily applied by the user.

It is another object of the present invention to provide a long-lasting mascara composition that colors human hair, such as eyelashes or eyebrows, without thickening them.

It is another object of the present invention to provide a long-lasting mascara composition that is resistant to water, e.g., is resistant to sweat, tears, or when worn while bathing or showering.

It is another object of the present invention to provide a long-lasting mascara that is natural-looking on application to human hair, such as eyelashes or eyebrows.

It is another object of the present invention to provide a new method for making up human hair, such as eyelashes or eyebrows.

It has now been discovered that these and other object that will become apparent from the description of the invention given hereinbelow are achieved by the use of a make-up composition according to the invention which, on application as a make-up product to human hair, such as eyelashes or eyebrows, stays on for more than one day, especially more than two days, and provided a natural-looking make-up result.

The Applicant has found that all of these objects are obtained with a wax-free composition comprising an aqueous dispersion of a particular film-forming acrylic polymer. The composition is easy to apply and coats the eyelashes well. After drying, the composition forms a smooth, uniform deposit. The make-up is not particularly loading, that is to say that it does not thicken the eyelashes. It provides a natural make-up result. The make-up is also comfortable and stays on well over time: the film does not wear away and the make-up deposited on the eyelashes and/or eyebrows stays on for more than one day, or even more than two days.

DETAILED DESCRIPTION OF THE INVENTION

Figure 1:
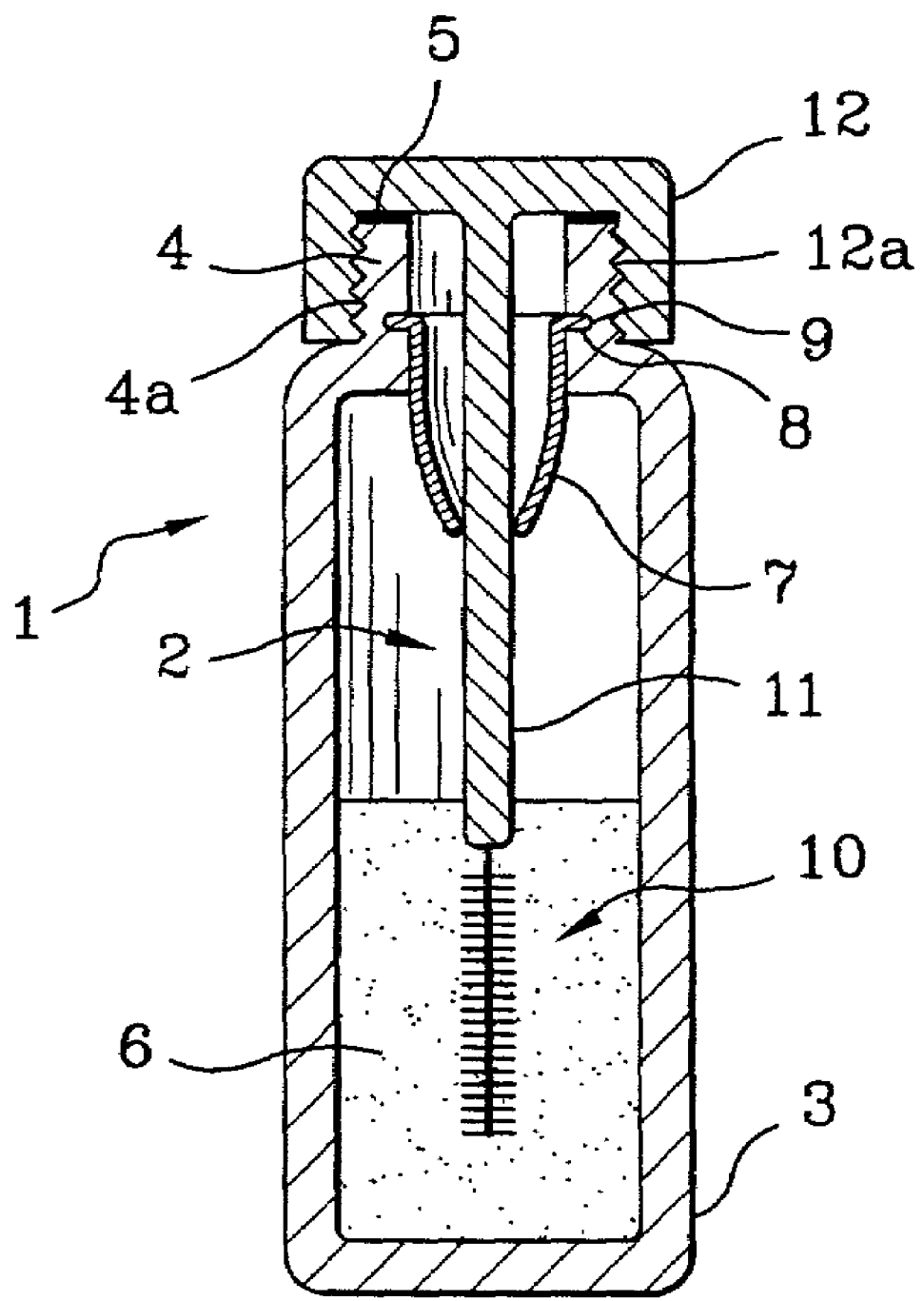
FIG. 1 is an elevation view of a mascara assembly in accordance with the invention.

One embodiment of the invention provides a wax-free mascara composition comprising, in a cosmetically acceptable aqueous medium, a film-forming acrylic polymer in the form of solid particles dispersed in the aqueous medium. The film-forming acrylic polymer used is capable of forming a film having a water-uptake, after immersion for 10 minutes in water at 25° C., of less than 25 weight percent (wt. %). The mascara composition has a viscosity, measured at 25° C., at a shear rate of 200 $s^{-1}$, ranging from 4 Pa·s to 18 Pa·s.

Another embodiment of the invention provides the use of a film-forming acrylic polymer as defined above, in a wax-free mascara composition having a viscosity, measured at 25° C., at a shear rate of 200 $s^{-1}$, ranging from 4 Pa·s to 18 Pa·s, to obtain a make-up result on human hair, such eyelashes or eyebrows, that stays on for more than one day, especially more than two days, and/or provides a natural make-up result.

The term "wax" used herein means a lipophilic fatty compound that is solid at room temperature (25° C.) and atmospheric pressure (760 mm Hg, i.e. $10^5$ Pa), with a reversible solid/liquid change of state, and having a melting point ranging from 30° C. to 200° C. By bringing the wax to its melting point, it is possible to make it miscible with oils and to form a microscopically homogeneous mixture. Upon returning the temperature of the mixture to room temperature, a recrystallization of the wax in the oils of the mixture is obtained. The melting point values correspond to the melting peak measured using a differential scanning calorimeter (D.S.C.) with a temperature rise of 5 or 10° C. per minute. The calorimeter sold under the name DSC 30 by the Mettler company may be used to measure these melting point values.

The composition according to the invention contains no wax as defined above: the compositions are "wax free." The term "wax free" as it is used herein means that while it is preferred that no wax whatsoever be present in the composition, it is possible to have very small amounts of wax in the compositions of the invention provided that these amounts do not materially affect at least one, preferably most, of the advantageous properties of the mascara of the invention.

The acrylic polymer used in the composition makes it possible to obtain a make-up product that stays on well over time, especially a make up that stays on for more than one day, or even two to three days, while exhibiting good water resistance.

According to the present invention, the water-uptake of the acrylic polymer is defined as the weight percentage of water absorbed by the acrylic polymer after immersion in water at 25° C. for 10 minutes. The water-uptake may be measured, for example, for a 300 µm thick layer of the film (where the thickness is measured before drying). The film is deposited on a plate and then dried for 24 hours at 30° C. and 50% relative humidity. Pieces having a size of about 1 cm$^2$ are cut from the dry film, weighed (to obtain mass measurement M1), and then immersed in water at 25° C. for 10 minutes. Each piece of film is then removed from the water, wiped to remove excess water from the surface of the film, and weighed (to obtain mass measurement M2).

The difference between M2 and M1 (M2-M1) is the amount of water absorbed by the polymer. The water-uptake is expressed as the percentage by weight of water relative to the weight of polymer, and may be calculated as follows: water-uptake=[(M2 −M1)/M1]×100. The test may be performed using one or a number of pieces of film.

In a preferred embodiment, the acrylic film-forming polymer used is capable of forming a film having a water-uptake of less than 25 wt. %, preferably, less than 20 wt. %, and most preferably less than 15 wt. %.

In another preferred embodiment, the acrylic polymer used is capable of forming a film having a hardness ranging from 8 to 40 seconds, preferably from 10 to 35 seconds, more preferably from 10 to 30 seconds, better still from 15 to 30 seconds and most preferably of from 20 to 30 seconds.

The hardness of the polymer film is measured as follows. A 300 µm thick (measured before drying) film is formed from an aqueous dispersion containing 40 wt. % solids of the free-radical polymer particles. The film is then dried for 24 hours at 30° C. and 50% relative humidity and the hardness of the dried film is measured according to ASTM standard D-43-66 or standard NF-T 30-016 (October 1981), using a Persoz pendulum.

The acrylic polymer used in the composition according to the invention may exhibit the water-uptake and/or film hardness properties defined above either by itself or in the presence of an auxiliary film-forming agent chosen from plasticizers and/or coalescers that are well known to those skilled in the art. In a preferred embodiment, an acrylic polymer exhibiting these water resistance and/or film hardness properties by itself is used.

The solid acrylic polymer particles dispersed in the aqueous medium used in the present composition generally have a size that can range from 10 nm to 200 nm, preferably ranging from 20 nm to 150 nm, and more preferably ranging from 50 nm to 100 nm.

The acrylic film-forming polymers that may be used according to the invention include those obtained from the polymerization of at least one monomer containing an ethylenic unsaturation, chosen from α,β-ethylenic carboxylic acids, α,β-ethylenic carboxylic acid esters, and α,β-ethylenic carboxylic acid amides, and combinations of two or more of these.

The α,β-ethylenic unsaturated carboxylic acids that may be used include acrylic acid, methacrylic acid, crotonic acid, maleic acid and itaconic acid. (Meth)acrylic acid and crotonic acid are preferably used. More preferably (meth) acrylic acid is used.

The α,β-ethylenic unsaturated carboxylic acid esters that may be used include (meth)acrylic acid esters (also known as (meth)acrylates), especially alkyl (meth)acrylates, in particular $C_1$-$C_{30}$, and preferably $C_1$-$C_{20}$, alkyl (meth)acrylates, aryl (meth)acrylates, in particular $C_6$-$C_{10}$ aryl (meth)acrylates, and hydroxyalkyl (meth)acrylates, in particular $C_2$-$C_6$ hydroxyalkyl (meth)acrylates.

Preferred alkyl (meth)acrylates that may be used include methyl methacrylate, ethyl methacrylate, butyl methacrylate, isobutyl methacrylate, 2-ethylhexyl methacrylate, lauryl methacrylate, and cyclohexyl methacrylate.

Preferred hydroxyalkyl (meth)acrylates that may be used include hydroxyethyl acrylate, 2-hydroxypropyl acrylate, hydroxyethyl methacrylate, and 2-hydroxypropyl methacrylate.

Preferred aryl (meth)acrylates that may be used include benzyl acrylate and phenyl acrylate. The (meth)acrylic acid esters that are particularly preferred are the alkyl (meth) acrylates.

It is, of course, possible to use a mixture of any of these monomers.

According to the present invention, the alkyl group of the esters may be either fluorinated or perfluorinated, i.e. some or all of the hydrogen atoms of the alkyl group may be substituted with fluorine atoms.

The carboxylic acid amides that may be used include, for example, (meth)acrylamides, and especially N-alkyl(meth) acrylamides including N-($C_2$-$C_{12}$ alkyl)(meth)acrylamides. N-alkyl(meth)acrylamides that may be used include N-ethylacrylamide, N-t-butylacrylamide, N-t-octylacrylamide and N-undecylacrylamide.

The acrylic film-forming polymers that may be used according to the invention may comprise, in addition to the monomers mentioned above, at least one styrene monomer, such as styrene or α-methylstyrene.

Acrylic polymers that may be used include those sold under the names "Syntran® 5190", "Syntran® 5760" and "Syntran® 5009" by the company Interpolymer, and "Dow Latex 424®" by the company Dow Chemical.

The aqueous acrylic polymer particles dispersion may be present in the composition of the invention in a content, as weight of solids, ranging from 5% to 60% by weight, relative to the total weight of the composition, preferably from 10% to 45% by weight, more preferably from 15% to 35% by weight, and most preferably from 20% to 35% by weight.

The cosmetically acceptable aqueous medium of the composition can comprise essentially of water. It can also comprise a mixture of water and one or more water-miscible solvents, such as lower $C_{1-5}$ monoalcohols, $C_3$-$C_4$ ketones, or $C_3$-$C_4$ aldehydes. The water-miscible solvent preferably used is ethanol. The content of water-miscible solvent can range from 0.1% to 15% by weight, preferably from 1% to 8% by weight, relative to the total weight of the composition.

Advantageously, the composition can have a viscosity ranging from 5 Pa·s (60 poises) to 15 Pa·s (150 poises), preferably from 6 Pa·s (70 poises) to 12 Pa·s (120 poises). Such viscosities allow fast and easy application of the composition and the formation of a uniform coating over the entire length of the human hair, e.g., the eyelashes or eyebrows.

The viscosity is measured at 25° C. with a Rheomat RM 180 viscometer fitted with a no. 4 rotor. The measurement is carried out after spinning the rotor for 10 minutes (after which time stabilization of the viscosity and the rotor spin speed is observed), at a shear rate of 200 s$^{-1}$.

One or more known thickeners can be used to give the composition of the invention the viscosity desired or required for application to keratin fibers, and in particular the eyelashes or eyebrows. Thickeners that can be used according to the invention include:

1. Water-soluble cellulose-based thickeners, such as hydroxyethylcellulose, methylcellulose, hydroxypropylcellulose and carboxymethylcellulose. Among these thickeners, mention may be made in particular of the gums sold under the name "Cellosize QP 4400 H" by the company Amerchol.
2. Guar gum, in particular those sold under the name Vidogum GH 175 by the company Unipectine and under the name Jaguar C by the company Meyhall.
3. Quaternized guar gum sold under the name Jaguar C-13-S by the company Meyhall.
4. Nonionic guar gums comprising $C_1$-$C_6$ hydroxyalkyl groups. Mention may be made, for example, of hydroxymethyl, hydroxyethyl, hydroxypropyl and hydroxybutyl groups. Such guar gums are sold in particular under the trade names Jaguar HP8, Jaguar HP60, Jaguar HP120 and Jaguar HP 105 by the company Meyhall, or under the name Galactasol 40H4FD2 by the company Aqualon.
5. Xanthan gum, carob gum, scleroglucan gum, gellan gum, rhamsan gum and karaya gum.
6. Alginates, maltodextrin, starch and its derivatives, hyaluronic acid and its salts.
7. Clays, and in particular montmorillonites, hectorites and laponites.
8. Crosslinked polyacrylic acids such as the Carbopol products from the company Goodrich.
9. The polyglyceryl (meth)acrylate polymers sold under the names Hispagel or Lubragel by the companies Hispano Quimica or Guardian.
10. Polyvinylpyrrolidone.
11. Polyvinyl alcohol.
12. Crosslinked acrylamide polymers and copolymers, such as those sold under the names "PAS 5161" or "Bozepol C" by the company Hoechst, "Sepigel 305" by the company SEPPIC, [lacuna] by the company Allied Colloid.
13. Crosslinked methacryloyloxyethyltrimethylammonium chloride homopolymers sold under the name "Salcare SC95" by the company Allied Colloid.
14. Associative polymers and, in particular, associative acrylic polymers.

The thickener(s) can be present in the composition of the invention in amounts effective for the composition to have the viscosity defined above. The thickener content can range, for example, from 0.1% to 10% by weight relative to the total weight of the composition, preferably from 0.5% to 5% by weight.

The composition can also comprise other ingredients usually used in cosmetics. Such ingredients can be chosen in particular from plasticizers, coalescers, fillers, dyestuffs such as pigments or colorants, surfactants, preserving agents, oils, cosmetic agents such as moisturizers and anti-UV agents which are well known in the prior art. Persons skilled in the art will know how to select these optional additives and/or the amounts to use, such that the advantageous properties of the make-up product are conserved.

Fillers that can be used in particular are the fillers usually used in mascara compositions. It is possible, for example, to use fumed silica, starch, such as rice starch, talc or polytetrafluoroethylene. The fillers can be present in the composition in a content ranging from 0.1% to 6% by weight relative to the total weight of the composition.

The composition can also comprise an auxiliary film-forming polymer, to allow the cosmetic and physicochemical properties of the film of make-up to be modified. This auxiliary film-forming polymer can be in dissolved form or in the form of solid particles dispersed in the aqueous medium of the composition. Auxiliary film-forming polymers that may be used, for example, are polycondensate polymers, for instance polyurethanes, or alternatively polyesters such as polyesters containing a sulphonic group. According to a preferred embodiment of the invention, the mascara composition does not contain, as film-forming polymer in the form of an aqueous dispersion, one or more acrylic polymer(s) as defined above.

The make-up composition according to the invention may be packaged in an applicator assembly comprising a reservoir, a removable means for closing the said reservoir, preferably in a leaktight manner, and a member for applying the composition to human hair, such as eyelashes and/or eyebrows.

Thus, another embodiment of the invention provides a mascara product comprising a reservoir containing a mascara composition of the invention, a member for applying the composition to human hair, such as eyelashes and/or eyebrows, and a removable closure means for closing the container.

The applicator member allows the composition to be taken up and allows the composition taken up to be deposited on the human hair, such as eyelashes and/or eyebrows. This applicator member is preferably integral with the leaktight closure means of the assembly.

The applicator assembly can also comprise a draining member (or drainer) for the applicator member. In another embodiment, the draining member is integral with the reservoir.

The applicator member can preferably be a mascara brush well known to those skilled in the art. Such a brush in particular comprises bristles arranged radially around a twisted core, in particular a metal core. The brush can be of varied shape and can comprise cutout sections. Mascara brushes are described, for example, in documents FR-A-2 607 373, EP-A-611 170, EP-A-811 336, EP-A-811 337 and EP-A-842 620, the content of which is incorporated into the present patent application by way of reference.

In another embodiment, the applicator assembly can comprise a reservoir containing a mascara composition as defined above, fitted with a neck and an applicator. The applicator can comprise a shaft fitted at a first end with an applicator member and integral with a second end of a handle component constituting a means for closing the applicator assembly.

The applicator assembly can also comprise an annular drainer fixed into the neck of the reservoir and through which the shaft passes, this drainer being capable of draining this shaft and/or the applicator member. Advantageously, this drainer is in the shape of a glove digit provided with a central passage orifice that can optionally be flocked. Such a device is described in particular in document FR-A-2 705 876.

The invention is illustrated in greater detail in the examples below.

FIG. 1 is an elevation view of a mascara assembly in accordance with the invention. With reference to FIG. 1, a mascara applicator assembly 1 can be seen, comprising an applicator 2 and a reservoir 3, fitted with a threaded neck 4 on which is mounted a leakproofing seal 5, containing a mascara composition 6 having the composition of Example 1. The reservoir 3 comprises in its neck 4 a drainer 7 held in place by means of a flange 8 that engages with a recess 9 also housed in the neck 4. The drainer is made, in a known manner, of a flexible, elastic material.

The applicator 2 comprises an applicator member 10 fixed to one end 11a of a shaft 11. A handle means 12 is integral with the end of the shaft 11 opposite the applicator member 10. The applicator member 10 is a mascara brush comprising, in a known manner, bristles distributed radially as a helical strip around a twisted core.

The handle means 12 forming a lid comprises threading 12a that engages with the threading 4a of the neck 4 of the reservoir 3. Leaktight closure of the reservoir 3 is obtained by screwing the handle means 10 onto the neck 4 of the reservoir fitted with the seal 5.

Examples of mascara compositions that can be packaged in the applicator assembly described above are given below.

EXAMPLES OF COMPOSITIONS

Example 1

A mascara having the composition below was prepared:

| | | |
|---|---|---|
| Aqueous dispersion of acrylic polymer containing 40% solids (Syntran ® 5190 from Interpolymer) | | 20.5 g AM |
| Hydroxyethyl cellulose (Cellosize QP 4400 H from Amerchol) | | 1.9 g |
| Fumed silica (Aerosil 200 from Degussa) | | 1 g |
| Ethanol | | 5 g |
| Propylene glycol | | 5 g |
| Pigments | | 5 g |
| Preserving agents | qs | |
| Water | qs | 100 g |

The aqueous dispersion of acrylic polymer "Syntran® 5190" forms a film having a water-uptake at 25° C., after immersion for 10 minutes in water, equal to 8%, the measurements being performed according to the protocols described previously.

The mascara applies easily to the eyelashes and gives a make-up result that stays on well for at least one day, or even two to four days, and that is resistant to rubbing with the fingers.

Example 2

A mascara having the composition below was prepared:

| | | |
|---|---|---|
| Aqueous dispersion of acrylic polymer containing 40% solids (Syntran ® 5760 from Interpolymer) | | 30 g AM |
| Hydroxyethyl cellulose (Cellosize QP 4400 H from Amerchol) | | 1.9 g |
| Ethanol | | 5 g |
| Propylene glycol | | 5 g |
| Pigments | | 5 g |
| Preserving agents | qs | |
| Water | qs | 100 g |

The aqueous dispersion of acrylic polymer "Syntran® 5760" forms a film having a water-uptake at 25° C., after immersion for 10 minutes in water, equal to 10%, the measurements being performed according to the protocols described previously.

The mascara applies easily and adheres well to the eyelashes. The make-up film coats the eyelashes well over their entire length and stays on well over time, for more than two days.

Obviously, numerous modifications and variations on the present invention are possible in light of the above teachings. It is therefore to be understood that within the scope of the appended claims, the invention may be practiced otherwise than a specifically described therein.

French patent application 0104886, filed Apr. 10, 2001, is incorporated herein, in its entirety, by reference, as are all documents, articles, patents, standards and references mentioned above.

The invention claimed is:

1. A wax-free mascara composition comprising solid particles of a film-forming acrylic polymer dispersed in a cosmetically acceptable aqueous medium, said film-forming acrylic polymer being capable of forming a film having a water-uptake, after immersion for 10 minutes in water at 25° C., of less than 25 wt. %, and said composition having a viscosity, measured at 25° C., at a shear rate of 200 s$^{-1}$, ranging from 4 Pa.s to 18 Pa.s, wherein said acrylic polymer is obtained by the polymerization of at least one monomer containing ethylenic unsaturation selected from the group consisting of α,β-ethylenic carboxylic acids, α,β-ethylenic carboxylic acid esters, α,β-ethylenic carboxylic acid amides, and mixtures thereof; and wherein said α,β-ethylenic unsaturated carboxylic acid amide is one member selected from the group consisting of N-ethylacrylamide, N-t-butylacrylamide, N-t-octylacrylamide, and N-undecylacrylamide.

2. The mascara composition of claim 1, wherein said acrylic polymer is capable of forming a film having a water-uptake of less than 20 wt. %.

3. The mascara composition of claim 1, wherein said acrylic polymer is capable of forming a film having a water-uptake of less than 15 wt. %.

4. The mascara composition of claim 1, wherein said acrylic polymer is capable of forming a film having a hardness, measured according to standard NF-T-30-016 using a Persoz pendulum, ranging from 8 to 40 seconds.

5. The mascara composition of claim 2, wherein said acrylic polymer is capable of forming a film having a hardness, measured according to standard NF-T-30-016 using a Persoz pendulum, ranging from 8 to 40 seconds.

6. The mascara composition of claim 3, wherein said acrylic polymer is capable of forming a film having a hardness, measured according to standard NF-T-30-016 using a Persoz pendulum, ranging from 8 to 40 seconds.

7. The mascara composition of claim 1, wherein said acrylic polymer is capable of forming a film having a hardness of from 10 to 35 seconds.

8. The mascara composition of claim 1, wherein said acrylic polymer is capable of forming a film having a hardness of from 10 to 30 seconds.

9. The mascara composition of claim 1, wherein said acrylic polymer particles are 10 nm to 200 nm in size.

10. The mascara composition of claim 1, wherein said acrylic polymer particles are 20 nm to 150 nm in size.

11. The mascara composition of claim 2, wherein said acrylic polymer particles are 20 nm to 150 nm in size.

12. The mascara composition of claim 1, wherein said acrylic polymer is present in said composition in an amount of 5 wt. % to 60 wt. % based on the total weight of said composition.

13. The mascara composition of claim 1, wherein said acrylic polymer is present in said composition in an amount of 10 wt. % to 45 wt. % based on the total weight of said composition.

14. The mascara composition of claim 1, wherein said acrylic polymer is present in said composition in an amount of 15 wt. % to 35 wt. % based on the total weight of said composition.

15. The mascara composition of claim 1, having a viscosity of from 5 Pa·s to 15 Pa·s.

16. The mascara composition of claim 1, having a viscosity of from 6 Pa·s to 12 Pa·s.

17. The mascara composition of claim 1, comprising at least one thickener.

18. The mascara composition according of claim 17, comprising at least one thickener selected from the group consisting of cellulose-based thickeners, guar gums, xanthan gum, carob gum, scleroglucan gum, gellan gum, rhamsan gum, karaya gum, alginates, maltodextrin, starch and its derivatives, hyaluronic acid and its salts, clays, crosslinked polyacrylic acids, polyglyceryl (meth)acrylates, polyvinylpyrrolidone, polyvinyl alcohol, crosslinked acrylamide polymers and copolymers, crosslinked methacryloyloxyethyltrimethylammonium chloride homopolymers, and associative polymers.

19. The mascara composition of claim 1, comprising at least one member selected from the group consisting of plasticizers, coalescers, fillers, dyestuffs, surfactants, preserving agents, oils, and cosmetic agents.

20. The mascara composition of claim 1, comprising at least one filler selected from the group consisting of fumed silica, starch, talc and polytetrafluoroethylene.

21. The mascara composition of claim 20, wherein said filler is present in an amount of from 0.1% to 6% by weight relative to the total weight of said composition.

22. The mascara composition of claim 1, comprising an auxiliary film-forming polymer.

23. A mascara product comprising a reservoir containing a mascara composition a removable closure means for closing said reservoir and a member for cosmetically applying said composition, wherein said mascara composition is a dye-free and wax-free mascara composition that lasts more than one day when applied to eyelashes, is resistant to water and wherein said mascara composition is a wax-free mascara composition comprising solid particles of a film-forming acrylic polymer dispersed in a cosmetically acceptable aqueous medium, said film-forming acrylic polymer being capable of forming a film having a water-uptake, after immersion for 10 minutes in water at 25° C., of less than 25 wt. %, and said mascara composition having a viscosity, measured at 25° C., at a shear rate of 200 s$^{-1}$, ranging from 4 Pa·s to 18 Pa·s.

24. The mascara product of claim 23, wherein said applicator member is integral with the removable closure means.

25. The mascara product of claim 23, wherein said applicator member is a mascara brush.

26. The mascara product of claim 23, further comprising a draining member.

27. A make-up product for use on human eyelashes or eyebrows, comprising a dye-free and wax-free mascara composition that lasts more than one day when applied to eyelashes, is resistant to water and wherein said mascara composition is a wax-free mascara composition comprising solid particles of a film-forming acrylic polymer dispersed in a cosmetically acceptable aqueous medium, said film-forming acrylic polymer being capable of forming a film having a water-uptake, after immersion for 10 minutes in water at 25° C., of less than 25 wt. %, and said mascara composition having a viscosity, measured at 25° C., at a shear rate of 200 s$^{-1}$, ranging from 4 Pa·s to 18 Pa·s.

28. A method for making-up human hair, comprising applying to said hair a dye-free and wax-free mascara composition that lasts more than one day when applied to eyelashes, is resistant to water, and wherein said mascara composition is a wax-free mascara composition comprising solid particles of a film-forming acrylic polymer dispersed in a cosmetically acceptable aqueous medium, said film-forming acrylic polymer being capable of forming a film having a water-uptake, after immersion for 10 minutes in water at 25° C., of less than 25 wt. %. and said mascara composition having a viscosity, measured at 25° C., at a shear rate of 200 s$^{-1}$, ranging from 4 Pa·s to 18 Pa·s.

29. A method for making-up human eyelashes according to claim 28.

30. A method for making-up human eyebrows according to claim 28.

* * * * *